(12) United States Patent
Davis

(10) Patent No.: US 8,916,208 B2
(45) Date of Patent: Dec. 23, 2014

(54) ALUMINOPHOSPHATE-BASED MATERIALS FOR THE TREATMENT OF WOUNDS

(75) Inventor: Mark E. Davis, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 356 days.

(21) Appl. No.: 11/159,561

(22) Filed: Jun. 22, 2005

(65) Prior Publication Data

US 2006/0039994 A1 Feb. 23, 2006

Related U.S. Application Data

(60) Provisional application No. 60/691,807, filed on Jun. 24, 2004.

(51) Int. Cl.
| | |
|---|---|
| A61K 33/42 | (2006.01) |
| A61K 33/06 | (2006.01) |
| A61P 17/02 | (2006.01) |
| A61L 26/00 | (2006.01) |

(52) U.S. Cl.
CPC ............ *A61K 33/42* (2013.01); *A61L 26/0004* (2013.01)
USPC ............ 424/601; 424/489; 424/602; 424/682

(58) Field of Classification Search
None
See application file for complete search history.

(56) References Cited

U.S. PATENT DOCUMENTS

| | | | |
|---|---|---|---|
| 4,310,440 | A | 1/1982 | Wilson et al. |
| 4,460,642 | A | 7/1984 | Errede et al. |
| 4,525,410 | A | 6/1985 | Hagiwara et al. |
| 4,775,585 | A | 10/1988 | Hagiwara et al. |
| 4,822,349 | A | 4/1989 | Hursey et al. |
| 5,374,411 | A | 12/1994 | Davis et al. |
| 5,470,585 | A | 11/1995 | Gilchrist |
| 5,556,699 | A | 9/1996 | Niira et al. |
| 5,965,264 | A | 10/1999 | Barenberg et al. |
| 6,004,667 | A | 12/1999 | Sakurada et al. |
| 6,083,602 | A | 7/2000 | Caldwell et al. |
| 6,514,306 | B1 | 2/2003 | Rohrbach et al. |
| 6,592,888 | B1 | 7/2003 | Jensen et al. |
| 2003/0133990 | A1 | 7/2003 | Hursey et al. |
| 2005/0058721 | A1 | 3/2005 | Hursey |

OTHER PUBLICATIONS

McCusker et al., Pure Appl. Chem.(2001), vol. 73, No. 2, pp. 381-394.*
Wan et al., J. Mater. Chem. (2000), vol. 10, pp. 2857-2862.*
Edinformatics.com-Math and Science Activity Center (1999), "Suspensions and Colloids".*
Stevenson, Australian Naturopathic Network (2002), "Haemostasis".*
Rodriguez et al. (1996), "Synthesis and Characterization of Molecular Sieve with AlPO$_4$-5 Framework. Preliminary Biomedical Essays." *Materials Letters*, 28:507-511.
Ahuja, et al. "Testing of Modified Zeolite Hemostatic Dressings in a Large Animal Model of Lethal Groin Injury," The Journal of TRAUMA: Injury, Infection and Critical Care (2006), 61(6):1312-1320.
Alam, et al. "Application of Zeolite Hemostatic Agent Achieves 100% Survival in a Lethal Model of Complex Groin Injury in Swine," The Journal of TRAUMA: Injury, Infection and Critical Care (2004), 56:974-983.
Alam, et al. "Hemorrhage Control in the Battlefield: Role of New Hemostatic Agents," Military Medicine (2005), 170(1):63-69.
Galownia, et al. "Aluminophosphate-based, microporous materials for blood clotting," Microporous and Mesoporous Materials (2006), 92:61-63.
Seyednejad, et al. "Topical haemostatic agents" British Journal of Surgery (2008), 95:1197-1225.
http://www.iza-structure.org—accessed Sep. 17, 2010 (6 pages).
Alam et al., "Application of a zeolite hemostatic agent achieves 100% survival in a lethal model of complex groin injury in swine," J. Trauma (2004) 56:974-983.
Alam et al., "Comparative analysis of hemostatic agents in a swine model of lethal groin injury," J. Trauma (2003) 54:1077-1082.
Davis et al., "A molecular sieve with eighteen-membered rings," Nature (1988) 331:698-699.
Flanigan, "Zeolites and molecular sieves: an historical perspective," in Introduction to Zeolite Science and Practice, Chap. 2, 2001, Elsevier, pp. 11-35.
Gramlich and Meier, "The crystal structure of hydrated NaA: A detailed refinement of a pseudosymmetric zeolite structure," Z. Kristallographie (1971) 133:134-149.
King, "Hemostatic dressings for the first responder: A review," Military Med. (2004) 169:716-720.
Kitao et al., "Theoretical studies on VPI-5. 3. The MS-Q force field for aluminophosphate zeolites," (1998) pp. 30-1-30-7, http://www.wag.caltech.edu/home-pages/tahir/vpi.htm.
Logar et al., "Recent developments in zeolite-like materials. Synthesis and characterization," Croatica Chemica Acta (1999) 72:187-208.
Pusateri et al., "Application of a granular mineral-based hemostatic agent (QuikClot) to reduce blood loss after grade V liver injury in swine," J. Trauma (2004) 57:555-562.
Tsutsumi et al., "Adsorbtion characteristics and surface free energy of AlPO$_4$-5," Colloid Polym. Sci. (1999) 277:83-88.
Wang et al., "Quantum sieving in carbon nanotubes and zeolites," Phys. Rev. Lett. (1999) 82:956-959.
Wilson et al., "Phosphate-based molecular sieves: novel synthetic approaches to new structures and compositions," in Introduction to Zeolite Science and Practice, Chap. 5B, 2001, Elsevier, pp. 229-260.
Wilson et al., "Aluminophosphate molecular sieves: a new class of microporous crystalline inorganic solids," J. Am. Chem. Soc. (1982) 104:1147-1149.
Wright et al., "Thermal injury resulting of application of a granular mineral hemostatic agent," J. Trauma (2004) 57:224-230.
VFI—Framework Type—P63/mcm, zeolites.ethz.ch/IZA-SC/Atlas_pdf/VFI.pdf, (2001).
Z-Medica, Quik Clot online brochure, "Saving lives through effective solutions to traumatic bleeding," www.z-medica.com, (2003).

* cited by examiner

*Primary Examiner* — Abigail Fisher
*Assistant Examiner* — Frank Choi
(74) *Attorney, Agent, or Firm* — Baker & Hostetler LLP

(57) ABSTRACT

A method is provided for promoting blood clotting. The area which is bleeding is contacted with an aluminophosphate molecular sieve. The molecular sieve preferably contains a substance which assists the clotting of blood. This substance is preferably $Ca^{2+}$ ions, which are readily introduced into aluminophosphate molecular sieves. Preferred aluminophosphate molecular sieves include $AlPO_4$-5 and VPI-5.

12 Claims, 2 Drawing Sheets

ALUMINOPHOSPHATE-BASED MATERIALS FOR THE TREATMENT OF WOUNDS

CROSS-REFERENCE TO RELATED APPLICATIONS

This application claims priority under 35 U.S.C. §119(e)(1) to Provisional U.S. Patent Application Ser. No. 60/691,807, filed Jun. 24, 2004. The disclosure of this provisional application is incorporated by reference in its entirety.

TECHNICAL FIELD

This invention relates generally to the use of porous materials to promote blood clotting, for example in the treatment of wound trauma.

BACKGROUND

A major way that trauma kills people is by breaking blood vessels and causing hemorrhage. The body is naturally able to overcome some amount of damage to blood vessels through blood clotting. Blood clotting occurs because of a number of enzymes which act in a cascade in response to damage to blood vessel walls or blood itself. Often, however, seriously injured people bleed too profusely for natural clotting to be able to stabilize their bleeding. A cycle can occur in which traumatic injury and blood loss produce acidosis and hypothermia, which in turn weaken the blood's ability to clot because of their effect on the reactions and enzymes that carry out blood clotting. There has consequently been research on ways to accelerate and facilitate the natural process of blood clotting.

U.S. Pat. No. 4,822,349 to Hursey et al. proposed the use of zeolite crystals in contact with blood to facilitate clotting. The mechanism suggested there was that the zeolite crystals would adsorb water from blood. It is known that zeolites have a large ability to absorb water, in part because they have a large surface area accessible to water molecules. It is also indicated in the Hursey et al. '349 patent that the heat generated by the exothermic reaction between zeolite material and moist blood would cauterize the wound.

U.S. Patent Publication No. 2003/0133990 to Hursey et al. made further proposals for the use of zeolite crystals in combination with other agents to facilitate clotting. A commercial zeolite-containing clotting accelerator called QuikClot (Z-Medica, Wallingford, Conn.) received FDA approval in 2002. QuikClot is a dehydrated powder comprised of a zeolite with the FAU topology and other inorganic solids. There have been various reports of experience with QuikClot.

It has been discovered that the use of QuikClot results in a temperature increase which may be problematic. For example, in James K. Wright et al., *J. Trauma*, 57, 224-30 (2004), it was reported that in experiments with anesthetized pigs, "[a]pplication of the agent [QuikClot] resulted in elevated tissue surface temperatures in excess of 95° C. and internal tissue temperatures exceeding 50° C., 3 mm deep to the bleeding surface." This effect is believed to be due to the fact that the adsorption of water onto zeolites is an exothermic process. For example, for zeolite A the enthalpy of adsorption has been reported to be on the order of −100 kJ/mol. Tsutsumi et al., *Colloid Polymer Sci.*, 277, 83-88 (1999).

As a way of dealing with the problem of heat release from products of the QuikClot type, it has been proposed to control the degree of hydration of the zeolite prior to applying it to tissue. This results in a lower degree of water absorption, which in turn limits the amount of heat generated. See in this regard U.S. Published Patent Application No. 2005/0058721.

There is therefore a need for a blood clotting accelerator which has the advantage of high adsorption of water achieved by the use of zeolites, but which does not release as much heat as zeolites do.

SUMMARY OF THE INVENTION

In an embodiment of the invention, a method is provided for promoting blood clotting. The blood is contacted with an aluminophosphate molecular sieve. Preferably, the molecular sieve comprises a substance which assists in the clotting of blood.

In a further embodiment of the invention, a wound kit is provided which comprises an aluminophosphate molecular sieve material and sterile packaging. Preferably, the molecular sieve comprises a substance which assists in the clotting of blood.

In a further embodiment of the invention, a method is provided for promoting blood clotting. The blood is contacted with a molecular sieve which has an enthalpy of adsorption of water whose magnitude is less than about 60 kJ/mol at physiological temperature.

DETAILED DESCRIPTION OF EMBODIMENTS OF THE INVENTION

Figure 1:
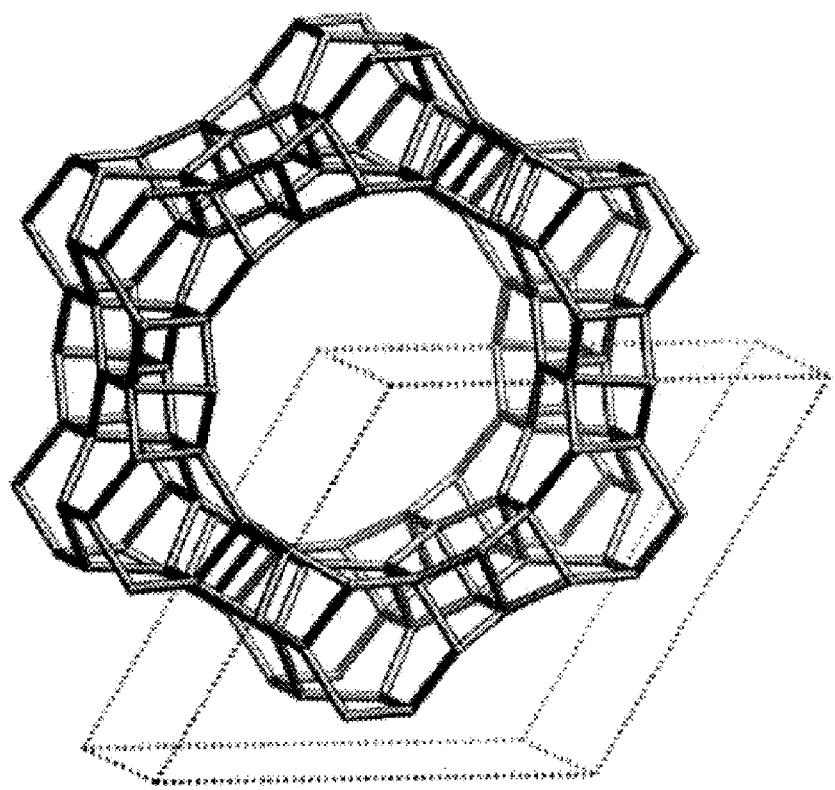
FIG. 1 (prior art) is a diagram of the structure of the VPI-5 molecular sieve.

Before describing the present invention in detail, it is to be understood that this invention is not limited to specific solvents, materials, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include both singular and plural referents unless the context clearly dictates otherwise. Thus, for example, reference to "a crystal" includes a plurality of crystals as well as a single crystal, reference to "a temperature" includes a plurality of temperatures as well as single temperature, and the like.

"Optional" or "optionally" means that the subsequently described circumstance may or may not occur, so that the description includes instances where the circumstance occurs and instances where it does not.

The term "zeolite" is applied to crystals comprising a framework of tetrahedrally-bonded aluminum and silicon atoms linked by oxygens. Such zeolites often have bound to them metal ions. Some zeolites are naturally occurring minerals, of which the earliest was discovered in the eighteenth century.

Zeolites belong to a category of materials which are called "molecular sieves" because the porosity inherent in their crystal structures allows limited passage of molecular species, somewhat similarly to the limited passage of macroscopic bodies through a sieve. An important characteristic often found in molecular sieves is that the surface area which they present to adsorbing small molecules is large, for example on the order of 100 $m^2$/g, because small molecules have access to the interior surfaces of the molecular sieve.

Over the years researchers have synthesized molecular sieves which are like zeolites with some aluminum or silicon atoms replaced by other substances such as phosphorus. See in this regard, for example, Stephen T. Wilson et al., *JACS*, 104, 1146-47 (1982) (announcing the synthesis of molecular sieves comprising phosphorus and aluminum). They have also synthesized molecular sieves which are like zeolites but contain few or no aluminum atoms, and instead comprise mostly silicon and oxygen atoms.

In more recent times, molecular sieves having crystal structures like those of zeolites have also come to be referred to as zeolites in an extended sense. They are often also called "zeolite-like materials." For a discussion of zeolites and zeolite-like materials in general, please refer to the *Handbook of Zeolite Science and Technology* (Scott M. Auerbach et al. eds., 2003).

An important characteristic of any zeolite-like material is its framework structure, that is to say, the spatial arrangement of the tetrahedrally-bonded (T) atoms, the oxygen atoms, and the bonds between T atoms and oxygen atoms. Zeolite framework structures are designated by three letter codes (e.g., CON, LTA, MFI) assigned by the International Zeolite Organization. Multiple different zeolites and zeolite-like materials of different T atom compositions can have the same zeolite framework structure. The framework structure of a molecular sieve is also often referred to as its "topology." Images of simplified representations of zeolite framework structures are available, together with much other information, from the Database of Zeolite Structures maintained by the International Zeolite Association.

The term "aluminophosphate molecular sieve" refers to a molecular sieve having a zeolite-like framework where at least some T atom positions are occupied by phosphorus atoms and by aluminum atoms. A wide variety of aluminophosphate molecular sieves are known. See in this regard, for example, Stephen T. Wilson, "Phosphate-based molecular sieves: novel synthetic approaches to new structures and compositions," in *Introduction to Zeolite Science and Practice* (H. van Bekkum et al. eds., 2d ed., Elsevier 2001). Aluminophosphate molecular sieves may contain silicon framework atoms, such molecular sieves often being referred to by the acronym SAPO. They may also contain a variety of other framework atoms in addition to aluminum and phosphorus.

Some examples of known aluminophosphate molecular sieves are the various molecular sieves designated by names beginning with AlPO, for example AlPO-5 (often also written $AlPO_4$-5), AlPO-8, AlPO-11, AlPO-14, AlPO-16, AlPO-21, AlPO-22, AlPO-25, AlPO-33, AlPO-41, AlPO-52, AlPO-C, AlPO-D, and AlPO-H2. Further examples are found among the molecular sieves designated with names beginning with SAPO, for example SAPO-5, SAPO-11, SAPO-31, and SAPO-41.

The term "adsorption" is often employed to describe the interaction of a molecular sieve with water or another fluid which becomes attached to its surfaces. The term "absorption" is also used in this context, because the water and other fluids commonly become attached to surfaces of the molecular sieve which are interior to the molecular sieve, and thus the water or other fluid enters the molecular sieve and is absorbed by it.

In an embodiment of the invention, a method is provided for promoting blood clotting. The blood is contacted with an aluminophosphate molecular sieve. Preferably, the molecular sieve comprises a substance which assists in the clotting of blood.

The aluminophosphate molecular sieve may be of any aluminophosphate structure. It may be a pure aluminophosphate or a SAPO or a molecular sieve with other types of framework atoms. Preferred structures include $AlPO_4$-5 and VPI-5. The structure of VPI-5 is shown in FIG. 1. As may be seen, VPI-5 has pores which are bounded by rings which contain eighteen framework atoms. These pores have a diameter of approximately 12.7 Å.

The aluminophosphate molecular sieve used in a method of the invention may have the particle size distribution with which it is synthesized. Alternatively, the molecular sieve may before contacting with blood be ground more or less finely or coarsely. A finer grinding may increase the blood volume absorbed per unit mass of molecular sieve. Some indication of the effect of grinding is given by the results of Example 2 below.

In general, an aluminophosphate molecular sieve may be expected to have a negative enthalpy of adsorption of water, indicating that the adsorption of water is an exothermic process so that the enthalpy of the product of the process (molecular sieve with water adsorbed) is less than the enthalpy of the starting materials (molecular sieve and water). An aluminophosphate molecular sieve should have an enthalpy of adsorption of water which has a smaller magnitude (absolute value) compared to the enthalpy for aluminosilicate zeolites, which is roughly on the order of $-100$ kJ/mol. Preferably the aluminophosphate molecular sieve used in the invention will have an enthalpy of adsorption of water whose magnitude is less than about 60 kJ/mol, more preferably less than about 50 kJ/mol. It is believed that in general aluminosilicate zeolites adsorb water by its attraction to charge-balancing cations found in the crystal framework, whereas the predominant mechanism for adsorption in aluminophosphate molecular sieves is dipole-dipole interaction and this method of adsorption has a lower energy. Aluminophosphates are distinguished among the crystalline microporous materials in regards to their water adsorption behavior.

In other embodiments of the invention, a microporous material is employed which has an enthalpy of adsorption which is sufficient low in magnitude, as for example, an enthalpy of adsorption of water whose magnitude is less than about 60 kJ/mol, more preferably less than about 50 kJ/mol.

The aluminophosphate molecular sieve is preferably sterile, for example because it is generally not desired to introduce any potentially contaminated material into an open wound. Standard techniques may be used to achieve sterilization, for example convective heating, autoclaving (possibly followed by drying to remove adsorbed water), or use of antimicrobial substances such as ethylene oxide.

As noted above, the molecular sieve preferably comprises one or more substances which assist in the clotting of blood. A wide variety of substances are known to have some positive effect on the clotting of blood. U.S. Patent Publication No. 2003/0133990 to Hursey et al. lists such substances and describes some test results obtained with such substances. Among the substances listed there are MgO, CaO, CeO, and $NaAlO_2$ as well as various types of silica gels. The substance which assists in the clotting may be an aid to clotting which is independently employed, as for example recombinant factor VIIa or the microfibrillar collagen hemostat sold under the name Avitene by Davol Inc. Naturally occurring substances involved in blood clotting such as fibrinogen and thrombin may be applied, somewhat as is done in "fibrin bandages" which are in limited use. Chitin and chitosan are also potential aids to clotting.

Preferably the substance which assists in the clotting of blood is one which influences the well-studied cascade of events in the blood clotting process. In particular, the calcium ion $Ca^{2+}$ is known to be required as a cofactor by enzymes which take part in the blood clotting process. Specifically, blood clotting begins with the formation of a substance called prothrombin activator. Two cascades, referred to as the intrinsic and extrinsic pathways, lead to the formation of prothrombin activator as a response to trauma to the blood vessel walls or the blood. It is believed that all steps in the extrinsic pathway and some steps in the intrinsic pathway require calcium ions for promotion or acceleration. For more information regarding the mechanism of blood clotting, the reader may refer to Arthur C. Guyton & John E. Hall, *Textbook of Medical Physiology* (10th ed., W. B. Saunders 2000), chapter 36.

Furthermore, in aluminophosphate molecular sieves $Ca^{2+}$ is in general readily taken up from solution, making it simple to prepare aluminophosphate molecular sieves which contain $Ca^{2+}$. When a molecular sieve with bound $Ca^{2+}$ is brought into contact with blood, it is believed that the $Na^+$ ions in blood ion-exchange with the $Ca^{2+}$ ions in the molecular sieve, thus resulting in a release of $Ca^{2+}$ which assists in the clotting process.

It may be desirable to apply the molecular sieve in such a way as to achieve complete coverage of the area which is bleeding. In connection with the methods of the invention, other known aids to the closing of bleeding wounds, such as the application of direct pressure to limit blood flow to the injured area, may also be helpful.

In a further embodiment of the invention, a wound kit is provided which comprises an aluminophosphate molecular sieve material and sterile packaging.

The wound kits of the invention may employ the aluminophosphate molecular sieves discussed above. Among these, as indicated above, the $AlPO_4$-5 and VPI-5 molecular sieves are particularly preferred. The molecular sieves may be processed as disclosed above, for example by grinding. Preferably, the molecular sieves of the wound kit contain a substance which assists in the clotting of blood, as disclosed above.

In the wound kits of the invention, packaging may be used which maintains the sterility of the molecular sieve prior to use. A sterility may be desired which is comparable to that for parenteral dosage forms. The packaging of the molecular sieve may be single-dose, such that once the package is opened sterility is no longer maintained and unused molecular sieve must be discarded. Advantageously the packaging could be constructed from flexible polyvinylchloride or polyolefin thermoplastics of the type used for packaging substantial volumes of intravenous solution. The molecular sieve could also be packaged, for example, in sterile stoppered glass or plastic containers. Antimicrobial additives could potentially be employed. If the primary package enclosing the molecular sieve is somewhat permeable to water, the packaging may desirably include an outer container whose purpose is to avoid exchange of water with the environment, allowing the molecular sieve to be maintained in its initial state of hydration. Reference is made to *Remington: the Science and Practice of Pharmacy* (20th ed., Alfonso R. Gennaro ed., Lippincott Williams & Wilkins 2000), chapters 40 and 41, for further information about the formulation of sterile dosage forms and their packages.

The wound kits of the invention may be provided with suitable instructions for use. They may be provided with suitable warnings, particularly if the packaging is designed for single-dose use. They may be provided with mechanisms for conveniently opening the packaging under field conditions. Preferably the kits are designed for use by first responders, and so they are able to be kept in a convenient fashion, for example, inside an ambulance or similar vehicle.

In the wound kits of the invention, the molecular sieve may be in the form of granules or a freely flowing powder to be spread over the bleeding area as needed. The packaging is in that case preferably designed to facilitate this spreading. For example, Franklin L. Wright et al., *J. Trauma*, 56, 205-08 (2004), reported the use of a Toomey syringe to apply Quik-Clot. Alternatively, the molecular sieve may be combined with a sterile dressing of some type and distributed within that dressing or on the surface of that dressing, so that the molecular sieve enters into contact with blood when the dressing is applied to a bleeding wound.

The following performance information is included herein to provide a further understanding of the inventive methods and kits for blood clotting. It is to be understood that this information is provided herein for the purposes of illustration only and is not to be interpreted as limiting the claimed invention in any way.

Table 1 lists the water absorption capacity, rate of water uptake, and total energy released for a number of fully dehydrated molecular sieve materials, including QuikClot. Details of how the data in this table were obtained are given in Example 1 below.

TABLE 1

Water absorption capacity rate of uptake and energy released from solids

| Sample | $cm^3$ liq. $H_2O$/g dry solid | Rate of $H_2O$ uptake (mg/min)* | Total energy released by $H_2O$ absorption (J/g $H_2O$) |
|---|---|---|---|
| QuikClot | 0.22 | 0.045 | 3737 |
| NaX | 0.31 | 0.055 | 3597 |
| SSZ-24 | 0.02 | nd** | 1478 |
| $AlPO_4$-5 | 0.19 | 0.056 | 2589 |
| VPI-5 | 0.24 | 0.050 | 2975 |
| VPI-5: $Ca^{2+}$ | 0.21 | 0.055 | 3040 |

*Rate of uptake for the initial mg of $H_2O$ absorption
**nd: not determined because amount was too low to obtain an accurate value Zeolite NaX (FAU topology) shows much higher capacity than QuikClot but similar energy release. Pure-silica SSZ-24 (AFI topology) reveals relatively little absorption, as expected, while $AlPO_4$-5 (AFI topology) has a large water uptake. Since these two materials have the same structure, the ability to absorb water is clearly a function of the composition. Note that the energy for the water absorption in $AlPO_4$-5 is lower than either QuikClot or NaX, as expected from the Tsutusmi et al. reference cited in the Background. Within the aluminophosphates, the water capacity of VPI-5 (VFI topology) is slightly larger than that of $AlPO_4$-5 (AFI topology), and the energies released from both $AlPO_4$-5 and VPI-5 are below 3000 J/g. When $Ca^{2+}$ ions are added to VPI-5, the absorption data are not significantly altered.

Table 2 shows data from clotting fresh mouse blood with QuikClot and VPI-5:$Ca^{2±}$.

TABLE 2

Blood clotting data for QuikClot and VPI-5.

| Sample | Mass of wet clotting agent (g) | Blood volume (mL) | Mass of dry clotting agent/volume of blood (mg/mL) | Clotting time (min.) | ΔT (° C.) |
|---|---|---|---|---|---|
| QuikClot | 0.28 | 0.5 | 0.48 | 0.5 | 7.9 |
| QuikClot (pulverized) | 0.34 | 0.8 | 0.36 | <1 | 10.0 |
| VPI-5: $Ca^{2+}$ | 0.30 | 0.6 | 0.39 | 1 | 4.7 |

Details of how the data in this table were obtained are given in Example 2 below.

Since QuikClot as received contains large particles, a pulverized sample was also prepared for better comparison to the free flowing VPI-5 powder. The pulverized QuikClot clots mouse blood slightly faster than VPI-5:$Ca^{2+}$, but does so with a temperature rise that is approximately double that of VPI-5:$Ca^{2+}$. The VPI-5:$Ca^{2+}$ is able to quickly clot mouse blood through the absorption of water and release of $Ca^{2+}$, and does so with a lower energy release than QuikClot. (VPI-5 alone does absorb water and gives approximately the same temperature increase but does not effectively clot.)

It is to be understood that while the invention has been described in conjunction with the preferred specific embodiments thereof, the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLE 1

Water Absorption by Molecular Sieves

Sodium exchanged zeolite X (FAU topology, Si/Al=1.25) was obtained from Strem Chemicals (Newburyport, Mass.) and used as received. SSZ-24 was synthesized as described in R.

Bialek, W. M. Meier, M. Davis and M. J. Annen, *Zeolites*, 438, 11 (1991). AlPO$_4$-5 was prepared according to known literature procedures using triethylamine as a template, as described in U.S. Pat. No. 4,440,871. Calcination was performed at 600° C. under dry flowing air. VPI-5 was synthesized as described in M. E. Davis and D. Young, *Stud. Surf Sci. Catal.*, 60, 53 (1991). Slow evaporation of a 2 mM solution of Ca(NO$_3$)$_2$·4H$_2$O (200 mL/g VPI-5) resulted in calcium ion containing VPI-5, VPI-5:$Ca^{2+}$.

Figure 2:
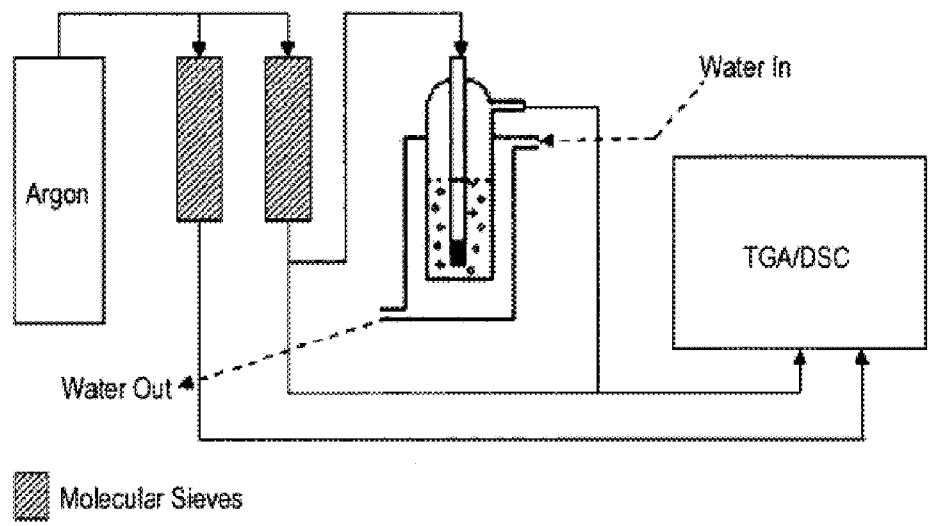
FIG. 2 is a schematic diagram of the apparatus used to determine absorption data.

Simultaneous thermogravimetric analyses and differential scanning calorimetry measurements were recorded on a modified Netzsch STA 449C Jupiter system, depicted in FIG. 2. UHP argon, 50 mL/min sample, 20 mL/min protective flow, were introduced to the sample chamber following dehydration over molecular sieves. Absorption measurements were obtained at 35° C. following in-situ sample dehydration. Water was added to the argon stream by passage through a jacketed bubbler at 25° C. just prior to the sample chamber. Silicates and aluminosilicates were dehydrated at 400° C. for 2 hours. Aluminophosphates were evacuated and backfilled twice prior to dehydration at 150° C. for 1 hour. Sample structures were verified before and after absorption measurements by X-ray diffraction using a Scintag XDS-2000 diffractometer equipped with a scintillation detector and CuKα radiation.

EXAMPLE 2

The Effect of Molecular Sieves on Blood Clotting

Blood clotting was performed in the apparatus in which samples were capable of being dehydrated according to the methods developed for absorption and backfilled with dry argon prior to introduction of mouse blood. Blood was drawn from live mice by heparinized needle to prevent pre-clotting during blood transfer and immediately introduced to the samples. The maximum temperature obtained was recorded using a RayTek ST80-XB infrared thermometer. Clotting was assessed visually and by inversion of the apparatus. Clot time was monitored by stopwatch.

I claim:

1. A method of promoting blood clotting from a wound, comprising contacting an aluminophosphate molecular sieve with the blood; and removing all or a portion of the aluminophosphate molecular sieve from the wound; wherein the contacting results in clotting of the blood, and wherein at least about 10% of the T positions in the framework of the aluminophosphate molecular sieve are occupied by phosphorus atoms.

2. The method of claim 1, wherein the aluminophosphate molecular sieve comprises a substance which assists in the clotting of blood.

3. The method of claim 2, wherein the substance which assists in the clotting of blood is a cofactor required by an enzyme which takes part in blood clotting.

4. The method of claim 3, wherein the substance which assists in the clotting of blood is $Ca^{2+}$.

5. The method of claim 1, wherein the aluminophosphate molecular sieve is finely ground.

6. The method of claim 1, wherein the aluminophosphate molecular sieve comprises atoms other than aluminum, oxygen, and phosphorus in its framework.

7. The method of claim 1, wherein the aluminophosphate molecular sieve is a VPI-5 molecular sieve.

8. The method of claim 1, wherein the aluminophosphate molecular sieve has an enthalpy of adsorption of water whose magnitude is less than about 60 kJ/mol at physiological temperatures.

9. The method of claim 1, further comprising a step of sterilizing the aluminophosphate molecular sieve.

10. The method of claim 1, wherein prior to contacting the aluminophosphate molecular sieve with the blood, the moisture content of the molecular sieve is adjusted to lie in a predetermined range.

11. The method of claim 1, wherein the blood which is clotted comprises blood flowing from a wound in an animal or human.

12. A method of promoting blood clotting from a wound, comprising contacting with the blood an aluminophosphate molecular sieve which an enthalpy of adsorption of water whose magnitude is less than about 60 kJ/mol at physiological temperatures and which comprises $Ca^{2+}$ ion; and removing all or a portion of the aluminophosphate molecular sieve from the wound; wherein the contacting results in clotting of the blood, and wherein at least about 10% of the T positions in the framework of the aluminophosphate molecular sieve are occupied by phosphorus atoms.

* * * * *